US008906049B2

(12) United States Patent
Chambers

(10) Patent No.: US 8,906,049 B2
(45) Date of Patent: Dec. 9, 2014

(54) DEVICE FOR TREATING HARDENED LESIONS AND METHOD OF USE THEREOF

(71) Applicant: Cook Medical Technologies LLC, Bloomington, IN (US)

(72) Inventor: Sean D. Chambers, Bloomington, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 0 days.

(21) Appl. No.: 13/971,348

(22) Filed: Aug. 20, 2013

(65) Prior Publication Data
US 2013/0338571 A1 Dec. 19, 2013

Related U.S. Application Data

(62) Division of application No. 12/837,834, filed on Jul. 16, 2010, now abandoned, which is a division of application No. 11/809,158, filed on May 31, 2007, now abandoned.

(51) Int. Cl.
A61B 17/22 (2006.01)
A61B 17/3207 (2006.01)
A61M 25/10 (2013.01)
A61B 17/00 (2006.01)
A61M 25/00 (2006.01)

(52) U.S. Cl.
CPC ...... *A61B 17/320725* (2013.01); *A61M 25/104* (2013.01); *A61M 2025/109* (2013.01); *A61M 2025/1086* (2013.01); *A61B 2017/22061* (2013.01); *A61B 2017/00539* (2013.01); *A61M 2025/105* (2013.01); *A61M 2025/1061* (2013.01); *A61B 2017/00778* (2013.01); *A61M 2025/1013* (2013.01); *A61M 2025/0057* (2013.01)

USPC .......................................... 606/159

(58) Field of Classification Search
CPC .............. A61M 25/104; A61M 25/10; A61M 25/1011; A61M 2025/1086; A61M 2025/105; A61M 2025/1075; A61M 2025/1072; A61M 2025/1013; A61M 2025/0057; A61M 2025/0093; A61M 37/0015; A61B 17/320758; A61B 17/12022; A61B 2017/00557; A61B 17/320725
USPC ............. 604/103.01, 103.02, 103.06, 103.08; 606/159, 170, 180, 191, 192, 194
See application file for complete search history.

(56) References Cited

U.S. PATENT DOCUMENTS 4,729,763 A 3/1988 Henrie
4,886,061 A 12/1989 Fischell et al.
(Continued)

FOREIGN PATENT DOCUMENTS

EP A 0117 519 2/1984
EP 0565 796 A1 10/1992
(Continued)

OTHER PUBLICATIONS

International Preliminary Report on Patentability—085150, May 29, 2009.

(Continued)

*Primary Examiner* — Jonathan W Miles
(74) *Attorney, Agent, or Firm* — Brinks Gilson & Lione

(57) ABSTRACT

A balloon catheter is provided that may be used to dilate hardened regions of a stenosis on a vessel wall. The balloon catheter is provided with cutting elements that extend along a surface of a balloon. At least one bioactive is present, either on the cutting element, within the interior of the balloon, within the material of the balloon or on an outside surface of the balloon. The bioactive is delivered to the vessel wall upon dilation of the balloon.

17 Claims, 4 Drawing Sheets

(56) References Cited

U.S. PATENT DOCUMENTS

| | | |
|---|---|---|
| 4,898,575 A | 2/1990 | Fischell et al. |
| 4,983,167 A | 1/1991 | Sahota |
| 5,019,042 A | 5/1991 | Sahota |
| 5,030,201 A | 7/1991 | Palestrant |
| 5,047,040 A | 9/1991 | Simpson et al. |
| 5,057,120 A | 10/1991 | Farcot |
| 5,078,723 A | 1/1992 | Dance et al. |
| 5,080,660 A | 1/1992 | Buelna |
| 5,090,958 A | 2/1992 | Sahota |
| 5,112,305 A | 5/1992 | Barath et al. |
| 5,147,377 A | 9/1992 | Sahota |
| 5,160,321 A | 11/1992 | Sahota |
| 5,181,920 A | 1/1993 | Mueller |
| 5,192,291 A | 3/1993 | Pannek, Jr. |
| 5,196,024 A | 3/1993 | Barath |
| 5,209,749 A | 5/1993 | Buelna |
| 5,224,945 A | 7/1993 | Pannek, Jr. |
| 5,224,949 A | 7/1993 | Gomeinger et al. |
| 5,320,605 A | 6/1994 | Sahota |
| 5,320,634 A | 6/1994 | Vigil |
| 5,336,178 A | 8/1994 | Kaplin et al. |
| 5,372,601 A | 12/1994 | Lary |
| 5,395,332 A | 3/1995 | Ressemann |
| 5,409,454 A | 4/1995 | Fischell et al. |
| 5,411,478 A | 5/1995 | Stillabowerer et al. |
| 5,431,673 A | 7/1995 | Summers |
| 5,441,510 A | 8/1995 | Simpson |
| 5,505,725 A | 4/1996 | Simpson |
| 5,556,408 A | 9/1996 | Farhat |
| 5,571,087 A | 11/1996 | Ressemann |
| 5,575,771 A | 11/1996 | Walinsky |
| 5,601,582 A | 2/1997 | Shelton et al. |
| 5,616,149 A | 4/1997 | Barath |
| 5,624,704 A | 4/1997 | Darouiche et al. |
| 5,628,746 A | 5/1997 | Clayman |
| 5,690,642 A | 11/1997 | Osborne et al. |
| 5,722,949 A | 3/1998 | Sanese |
| 5,728,129 A | 3/1998 | Summers |
| 5,779,698 A | 7/1998 | Clayman et al. |
| 5,792,158 A | 8/1998 | Lary |
| 5,797,935 A | 8/1998 | Barath |
| 5,814,061 A | 9/1998 | Osborne et al. |
| 5,830,217 A | 11/1998 | Ryan |
| 5,904,679 A | 5/1999 | Clayman |
| 5,910,144 A | 6/1999 | Hayashi |
| 5,921,958 A | 7/1999 | Ressemann et al. |
| 6,033,380 A | 3/2000 | Butaric et al. |
| 6,036,689 A | 3/2000 | Tu et al. |
| 6,036,708 A | 3/2000 | Sciver |
| 6,071,285 A | 6/2000 | Lashinski et al. |
| 6,123,718 A | 9/2000 | Tu et al. |
| 6,165,187 A | 12/2000 | Reger |
| 6,197,013 B1 | 3/2001 | Reed et al. |
| 6,231,572 B1 | 5/2001 | Hart et al. |
| 6,245,040 B1 | 6/2001 | Inderbitzen et al. |
| 6,280,464 B1 | 8/2001 | Hauashi |
| 6,283,947 B1 | 9/2001 | Mirzaee |
| 6,306,151 B1 | 10/2001 | Lary |
| 6,355,013 B1 | 3/2002 | Van Muiden |
| 6,371,961 B1 | 4/2002 | Osborne et al. |
| 6,500,186 B2 | 12/2002 | Lafontaine et al. |
| 6,565,583 B1 * | 5/2003 | Deaton et al. .................. 606/159 |
| 6,569,441 B2 * | 5/2003 | Kunz et al. ..................... 424/423 |
| 6,632,231 B2 | 10/2003 | Radisch |
| 6,656,155 B2 * | 12/2003 | Freyman .................. 604/103.01 |
| 6,695,830 B2 * | 2/2004 | Vigil et al. ..................... 604/509 |
| 6,746,463 B1 | 6/2004 | Schwartz |
| 6,808,531 B2 | 10/2004 | Lafontaine et al. |
| 6,855,124 B1 | 2/2005 | Gonzalez |
| 7,279,002 B2 | 10/2007 | Shaw |
| 2003/0028212 A1 | 2/2003 | Saab |
| 2003/0114877 A1 | 6/2003 | Gellman |
| 2003/0144683 A1 * | 7/2003 | Sirhan et al. .................. 606/194 |
| 2004/0073297 A1 | 4/2004 | Rohde et al. |
| 2004/0122465 A1 | 6/2004 | McMurtry et al. |
| 2004/0133223 A1 | 7/2004 | Weber |
| 2004/0143287 A1 | 7/2004 | Konstantino et al. |
| 2004/0193196 A1 | 9/2004 | Appling et al. |
| 2004/0199191 A1 | 10/2004 | Schwartz |
| 2004/0243158 A1 | 12/2004 | Konstantino et al. |
| 2005/0021070 A1 | 1/2005 | Feld et al. |
| 2005/0021071 A1 | 1/2005 | Konstantino et al. |
| 2005/0288629 A1 | 12/2005 | Kunis |
| 2006/0111736 A1 | 5/2006 | Kelley |
| 2006/0173487 A1 | 8/2006 | Uflacker et al. |
| 2007/0073329 A1 | 3/2007 | Hardert |
| 2007/0106215 A1 | 5/2007 | Olsen |
| 2007/0135789 A1 | 6/2007 | Chang et al. |

FOREIGN PATENT DOCUMENTS

| | | |
|---|---|---|
| EP | 09760363 A2 | 7/1999 |
| WO | WO 95/26776 | 10/1995 |
| WO | WO2004/066852 | 8/2004 |

OTHER PUBLICATIONS

Delphion printout—English title and abstract for EPA 0 117 519—1 page, Dec. 6, 2007.

* cited by examiner

DEVICE FOR TREATING HARDENED LESIONS AND METHOD OF USE THEREOF

RELATED APPLICATIONS

The present patent application is a division of U.S. patent application Ser. No. 12/837,834, filed Jul. 16, 2010 which is a division of U.S. patent application Ser. No. 11/809,158, filed May 31, 2007. The contents of the prior applications are hereby incorporated by reference.

FIELD OF THE INVENTION

The present invention relates generally to medical devices including a bioactive and more particularly to balloon catheters used to dilate narrowed portions of a vessel having a hardened lesion.

BACKGROUND

Balloon catheters are widely used in the medical profession for various intraluminal procedures. One common procedure involving the use of a balloon catheter relates to angioplasty dilation of coronary or other arteries suffering from stenosis (i.e., a narrowing of the arterial lumen that restricts blood flow).

Although balloon catheters are used in many other procedures as well, coronary angioplasty using a balloon catheter has drawn particular attention from the medical community because of the growing number of people suffering from heart problems associated with stenosis. This has lead to an increased demand for medical procedures to treat such problems. Angioplasty procedures have become a popular alternative for treating coronary stenosis because angioplasty procedures are considerably less invasive than other alternatives. For example, stenosis of the coronary arteries has traditionally been treated with bypass surgery. In general, bypass surgery involves splitting the chest bone to open the chest cavity and grafting a replacement vessel onto the heart to bypass the blocked, or stenosed, artery. However, coronary bypass surgery is a very invasive procedure that is risky and requires a long recovery time for the patient.

To address the increased need for coronary artery treatments, the medical community has turned to angioplasty procedures, in combination with stenting procedures, to avoid the problems associated with traditional bypass surgery. Typically, angioplasty procedures are performed using a balloon-tipped catheter that may or may not have a stent mounted on the balloon (also referred to as a stented catheter). The physician performs the angioplasty procedure by introducing the balloon catheter into a peripheral artery (commonly one of the leg arteries) and threading the catheter to the narrowed part of the coronary artery to be treated. During this stage, the balloon is deflated and collapsed onto the shaft of the catheter in order to present a low profile which may be passed through the arterial lumens.

Once the balloon is positioned at the narrowed part of the artery, the balloon is expanded by pumping a mixture of saline and contrast solution through the catheter to the balloon. As a result, the balloon presses against the inner wall of the artery to dilate it. If a stent is mounted on the balloon, the balloon inflation also serves to expand the stent and implant it within the artery. After the artery is dilated, the balloon is deflated so that it once again collapses onto the shaft of the catheter. The balloon-tipped catheter is then retracted from the arteries. If a stent is mounted on the balloon of the catheter, the stent is left permanently implanted in its expanded state at the desired location in the artery to provide a support structure that prevents the artery from collapsing back to its pre-dilated condition. On the other hand, if the balloon catheter is not adapted for delivery of a stent, either a balloon-expandable stent or a self-expandable stent may be implanted in the dilated region in a follow-up procedure.

Although the treatment of stenosed coronary arteries is one common example where balloon catheters have been used, many other uses are also possible. For example, balloon catheters can have application in the treatment of blockages of the peripheral blood vessels, esophagus, trachea, colon, biliary tract, urinary tract and at other locations in the body. Other applications include the treatment of carotid artery stenosis, the narrowing of the carotid arteries, which are the main arteries in the neck that supply blood to the brain. Carotid artery stenosis (also called carotid artery disease) is a relatively high risk factor for ischemic stroke. The narrowing is usually caused by plaque build-up in the carotid artery. Plaque forms when cholesterol, fat and other substances form in the inner lining of an artery. This formation is called atherosclerosis.

One problem that may be encountered with conventional angioplasty techniques is the proper dilation of stenosed regions that are hardened and/or have become calcified. Stenosed regions may become hardened for a variety of reasons, such as the buildup of atherosclerotic plaque or other substances. Hardened regions of stenosis can be difficult to completely dilate using conventional balloons because hardened regions tend to resist the expansion pressures applied by conventional balloon catheters.

Angioplasty cutting devices offer a method of treating hardened regions. Such devices include an angioplasty balloon having one of more cutting surfaces present on the balloon surface. Upon expansion of the balloon, the cutting surfaces are configured to contact the hardened vessel wall and to break the plague, allowing further expansion of the vessel. One such cutting device is disclosed in U.S. publication number 2006/0173487A1, published Aug. 3, 2006.

While angioplasty presently enjoys wide use, it suffers from two major problems. First, the blood vessel may suffer acute occlusion immediately after or within the initial hours after the dilation procedure. Such occlusion is referred to as "abrupt closure." Abrupt closure occurs in perhaps five percent or so of the cases in which angioplasty is employed, and can result in myocardial infarction and death if blood flow is not restored promptly. The primary mechanisms of abrupt closures are believed to be elastic recoil, arterial dissection and/or thrombosis. It has been postulated that the delivery of an appropriate agent (such as an antithrombotic) directly into the arterial wall at the time of angioplasty could reduce the incidence of thrombotic acute closure, but the results of attempts to do so have been mixed.

A second major problem encountered in angioplasty is the re-narrowing of an artery after an initially successful angioplasty. This re-narrowing is referred to as "restenosis" and typically occurs within the first six months after angioplasty. Restenosis is believed to arise through the proliferation and migration of cellular components from the arterial wall, as well as through geometric changes in the arterial wall referred to as "remodeling."

The delivery of appropriate bioactives directly into the arterial wall offers a route to interrupt the cellular and/or remodeling events leading to restenosis. Drug coated stent devices have been employed for this purpose. For example, stents coated with sirolimus, paclitaxel or similar drugs have been employed for this purpose.

It would be also be desirable to develop non-stenting devices and methods for reliably delivering suitable bioactives directly into a body portion during or following balloon angioplasty, so as to treat or prevent such conditions and diseases, for example, to prevent abrupt closure and/or restenosis of a body portion such as a passage, lumen or blood vessel. As a particular example, it would be desirable to have devices and methods which can deliver an antithrombic or other medication to the region of a blood vessel which has been treated by angioplasty.

SUMMARY

A balloon catheter is provided that may be used to dilate a vessel wall having hardened regions and to deliver a bioactive to the vessel wall. The balloon catheter includes an expandable balloon and a cutting device having at least one cutting element extending along a surface of the balloon. At least one bioactive is present, either on the cutting element, within the interior of the balloon, within the material of the balloon or on an outside surface of the balloon. The bioactive is delivered to the vessel wall upon dilation of the balloon.

One embodiment of the present invention provides a balloon catheter including a shaft having a distal end and a proximal end and an expandable balloon mounted at the distal end of the shaft. The shaft has an inflation lumen extending therethrough and in fluid communication with an interior region of the balloon. At least a length of an outer surface of the balloon has a working surface adapted to dilate a vessel wall. The balloon catheter also includes a cutting device having at least one cutting element that contacts the outer surface of the balloon when the balloon is in an expanded state. A composition including a bioactive is present on at least a portion of the cutting element.

In one embodiment the cutting device also includes a proximal coil and a distal coil. A middle portion of the cutting element extends along the outer surface of the balloon at the working surface. The proximal end of the cutting element is affixed to the proximal coil, which proximally extends from the working surface to the shaft. The distal end of the cutting element is affixed to the distal coil, which distally extends from the working surface of the balloon to the shaft. The proximal and the distal coils are affixed to the shaft.

In another embodiment, the cutting device includes a plurality of cutting elements.

In yet another embodiment, the bioactive is releasibly attached to the cutting element.

In another embodiment, the composition also includes a bioabsorbable material.

In yet another embodiment, the bioactive is selected from paclitaxel, rapamycin, a rapamycin derivative, an antisense oligonucleotide, or a mTOR inhibitor.

In another embodiment, the cutting element includes stainless steel, nickel, silver, platinum, palladium, gold, titanium, tantalum, iridium, tungsten, a super-elastic nickel titanium alloy, or inconel.

Another embodiment of the present invention provides a balloon catheter including a shaft having a distal end and a proximal end and an expandable balloon mounted at the distal end of the shaft. The shaft has an inflation lumen extending therethrough and in fluid communication with an interior region of the balloon. At least a length of an outer surface of the balloon includes a working surface adapted to dilate a vessel wall. The balloon catheter also includes a cutting device having at least one cutting element attached to the outside surface of the balloon and having at least one channel providing a fluid path between the interior of the balloon and an exterior surface of the balloon. In another embodiment, an inflation fluid is contained the balloon and a composition including a bioactive is present within the inflation fluid.

Another embodiment of the present invention provides a balloon catheter including a shaft having a distal end and a proximal end and an expandable balloon mounted at the distal end of the shaft. The shaft has an inflation lumen extending therethrough and in fluid communication with an interior region of the balloon. At least a length of an outer surface of the balloon includes a working surface adapted to dilate a vessel wall. The balloon includes at least one pore providing fluid communication between the interior region of the balloon and the outer surface of the balloon. The balloon catheter also includes a cutting device having at least one cutting element contacting the outer surface of the balloon when the balloon is in an expanded state. A composition including a bioactive is present on at least a portion of the cutting element.

Another aspect of the present invention provides method of delivering a bioactive to a vessel wall. The method includes positioning an expandable balloon portion of a balloon catheter at a site within a vessel. The balloon catheter includes a shaft having a distal end and a proximal end and an expandable balloon mounted at the distal end of the shaft. The shaft has an inflation lumen extending therethrough and in fluid communication with an interior region of the balloon. At least a length of an outer surface of the balloon has a working surface adapted to dilate a vessel wall. The balloon catheter also includes a cutting device having at least one cutting element that contacts the outer surface of the balloon when the balloon is in an expanded state. A composition including a bioactive is present on at least a portion of the cutting element.

The method also includes expanding the balloon to cause the cutting element to contact the vessel wall and to dilate the vessel wall, and maintaining contact with the vessel wall for a time sufficient to deliver a therapeutically effective amount of bioactive to the vessel wall.

BRIEF DESCRIPTION OF THE DRAWINGS

The invention may be more fully understood by reading the following description in conjunction with the drawings, in which.

DEFINITIONS

Figure 1:
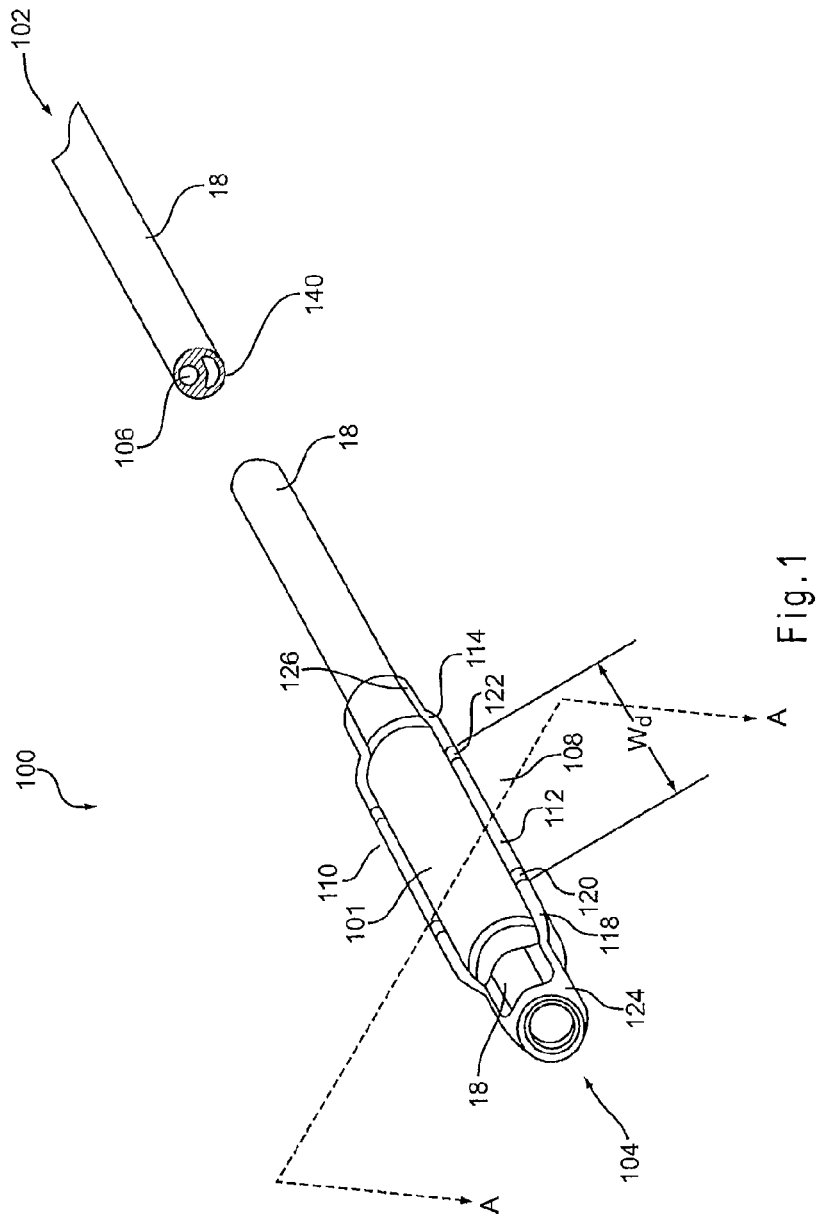
FIG. 1 is a side elevational view of a balloon catheter with cutting elements extending along the balloon.

Unless otherwise defined, all technical and scientific terms used herein have the same meaning as commonly understood by one of ordinary skill in the art to which this invention pertains. In case of conflict, the present document, including definitions, will control. Preferred methods and materials are described below, although methods and materials similar or equivalent to those described herein can be used in the practice or testing of the present invention. The materials, methods, and examples disclosed herein are illustrative only and not intended to be limiting.

As used herein the terms "comprise(s)," "include(s)," "having," "has," "can," "contain(s)," and variants thereof, are intended to be open-ended transitional phrases, terms, or words that do not preclude the possibility of additional acts or structures. The present invention also contemplates other embodiments "comprising," "consisting of" and "consisting essentially of," the embodiments or elements presented herein, whether explicitly set forth or not.

The term "biocompatible" material refers to a material that is compatible with living tissue or a living system by not being toxic or injurious and not causing immunological rejection.

The term "biodegradable" material refers to a material that dissipates upon implantation within a body, independent of the mechanisms by which dissipation can occur, such as dissolution, degradation, absorption and excretion. The actual choice of which type of materials to use may readily be made by one of ordinary skill in the art. Such materials are often referred to by different terms in the art, such as "bioresorbable," "bioabsorbable," or "biodegradable," depending upon the mechanism by which the material dissipates. The prefix "bio" indicates that the erosion occurs under physiological conditions, as opposed to other erosion processes, caused for example, by high temperature, strong acids or bases, UV light or weather conditions.

The term "controlled release" refers to the release of an agent at a predetermined rate. A controlled release may be constant or vary with time. A controlled release may be characterized by a drug elution profile, which shows the measured rate that the agent is removed from a device in a given solvent environment as a function of time. For example, a controlled release elution profile from a medical device may include an initial burst release associated with the deployment of the valve prosthesis, followed by a more gradual subsequent release. A controlled release may be a gradient release in which the concentration of the agent released varies over time or a steady state release in which the agent is released in equal amounts over a certain period of time (with or without an initial burst release).

As used herein, a "barrier layer" is any layer that is placed over at least a portion of a bioactive present in or on a portion of a device of the present invention. In general, the bioactive will not be present in the barrier layer. Any mixing of a bioactive with the barrier layer is unintentional and merely incidental. The barrier layer may or may not be the outer-most layer present on the device. For example, a bioactive may be coated onto a surface of the device, a first barrier layer placed over the bioactive and further barrier layers and layers contain the same or a different bioactive placed on the first barrier layer. The barrier layer may control the release of the bioactive from the device upon implantation.

As used herein, a "carrier material" refers to a material that forms a mixture with bioactive on or in a device of the present invention. The carrier material may control the release of the bioactive from the device.

As used herein, the term "bioactive" refers to any pharmaceutically active agent that produces an intended therapeutic effect on the body to treat or prevent conditions or diseases.

The term "treatment" or "treating" as used herein describes the management and care of a human or veterinary patient for the purpose of combating or preventing a disease, condition, or disorder and includes the administration of a bioactive to alleviate the symptoms or complications, or eliminate the disease, condition, or disorder.

A "therapeutically-effective amount" as used herein is the minimal amount of a bioactive which is necessary to impart therapeutic benefit to a human or veterinary patient. For example, a "therapeutically effective amount" to a human or veterinary patient is such an amount which induces, ameliorates or otherwise causes an improvement in the pathological symptoms, disease progression or physiological conditions associated with or resistance to succumbing to a disorder, for example restenosis.

DETAILED DESCRIPTION

For the purposes of promoting an understanding of the principles of the invention, reference will now be made to the embodiments illustrated in the drawings and specific language will be used to describe the same. It will nevertheless be understood that no limitation of the scope of the invention is thereby intended, and alterations and modifications in the illustrated device, and further applications of the principles of the invention as illustrated therein are herein contemplated as would normally occur to one skilled in the art to which the invention relates.

The present invention generally provides a balloon catheter including an expandable balloon and a cutting device, at least one of which incorporates at least one bioactive. The balloon catheter can be used to dilate hardened regions of a stenosis in a body vessel. In one embodiment, the bioactive is present on at least a portion of the cutting device. In such an embodiment, the bioactive is delivered to the surface of the vessel as a result of the contacting of the cutting device with the vessel surface.

In other embodiments, the bioactive is present on an outside surface of the balloon or is contained within the balloon. In certain embodiments where the bioactive is contained within the balloon at least a portion of the surface of the balloon is at least semi-permeable to the bioactive so that the bioactive can be delivered through the balloon to the vessel wall. Alternatively, a portion of the cutting device can contain channels providing a delivery path between the interior of the balloon and the external surface of the device.

The Cutting Device

The cutting device provides at least one cutting element and a mechanism for positioning the cutting element on the surface of an expandable balloon. The cutting element is position so that, upon at least partial expansion of the balloon within a vessel, this element contacts any stenotic lesion present to lacerate this lesion to assist in breaking up any plaque and allow for expansion of the vessel. In one embodiment, the cutting device takes the form of one or more blades attached to a portion of the outside surface of the balloon. The blades may be attached to the balloon by a variety of means. For example, the blades may be attached by adhesive or by mechanical attachment, for example, by clips or fasteners. Alternatively, one or more blades can be partially imbedded into the material of the balloon.

In other embodiments, the cutting device is not fixed to the balloon but is instead free to move relative to the surface of the balloon. In such embodiments, portions of the cutting device can move relative to the balloon surface during the expansion and contraction of the balloon. The absence of a rigid region attaching the cutting device to the balloon surface can result in a balloon that is more flexible and hence improve the ability of the balloon to expand and collapse. In certain such embodiments, the cutting device includes one or more wires spaced over an external surface of the balloon and constrained at the proximal and distal ends of the balloon.

FIG. 1 illustrates one embodiment of a balloon catheter of the present invention. The catheter includes a catheter shaft 18 extending from a proximal end 102 to a distal end 104 and an inflation lumen 106 extending from near the proximal end to near the distal end. A balloon 101 is mounted at the distal end 104 of the shaft and inflation lumen 106 is in fluid communication with the interior of the balloon. Four cutting elements, of which cutting elements 108 and 110 are shown, overlay the outside surface of the balloon and extend from near the distal end of the balloon to near the proximal end of the balloon. Catheter shaft 18 can also include one or more additional lumen, such as lumen 140.

The outer surface of the balloon 101 has a working surface that extends along portion $W_d$ of the length of the balloon 101. The working surface is that portion of the balloon surface that contacts the vessel wall upon inflation of the balloon. The length $W_d$ of the working surface is the distance between the balloon proximal end, where a tapered proximal portion of the balloon meets the region that contacts the vessel wall, and the balloon distal end, where the tapered distal portion of the balloon meets the region that contacts the vessel wall. The working surface of the balloon 101 may be connected to shaft 18 with the tapered proximal portion and the tapered distal portion of the balloon 101. Typically, the working surface of the balloon 101 is a portion that inflates to a generally uniform circumference in order to evenly dilate a section of a lumen. However, the working surface does not necessarily need to have a uniform circumference.

The structure of the cutting elements will now be illustrated with reference to cutting element 108. Cutting element 108 includes central portion 112 overlaying the working surface of balloon 101, distal end portion 118 and proximal end portion 114. Central portion 112 is attached to distal end portion 118 at joint 120 and to proximal end portion 114 at joint 122. Joints 118 and 120 may be any kind of joint known in the art, for example an adhesive or solder joint. The present invention also includes embodiments where the central and end portions of the cutting element are continuous and no joints are required.

The distal end of distal end portion is attached to collar 124, which surrounds the distal end of shaft 18. The proximal end of proximal end portion 114 is attached to collar 126, which surrounds shaft 18 at the proximal end of balloon 101. Of course, the present invention also completes that additional cutting elements can overlay balloon 101 in a manner similar to cutting elements 108 and 110. In various embodiments, three, four, five, six or more cutting elements may be present.

The present invention also includes embodiments where portions of the one or more cutting elements are not parallel to the axis of shaft 18 (non-axial elements). For example, one or more cutting elements may overlay balloon 101 in a helical, a serpentine or other form. In one embodiment, the cutting element circumvents the working surface one of more times in a helical form. In various embodiments, the cutting elements circumvent the working surface one, two, three, four, five, or more times.

The present invention also includes embodiments where the cutting elements include a mechanism to allow a lengthening or realignment of the cutting element upon expansion of balloon 101. In one embodiment, at least one of collars 124 and 126 is free to rotate and/or to move along the axis of shaft 18 to accommodate for the expansion of balloon 101 and for any foreshortening of balloon 101 as the balloon expands. In another embodiment, the cutting elements are portioned in a helical form circumventing balloon 101 and partially uncoil to accommodate expansion of the balloon. In yet other embodiments, at least a portion of the cutting device includes a secondary structure, such as a coil, which allows for linear expansion of that portion. For example, at least one of distal end portion 118 and proximal end portion 114 may include a coiled portion to accommodate expansion of balloon 101. In yet other embodiments, the cutting device is at least partially formed of an expandable material.

Figure 2:
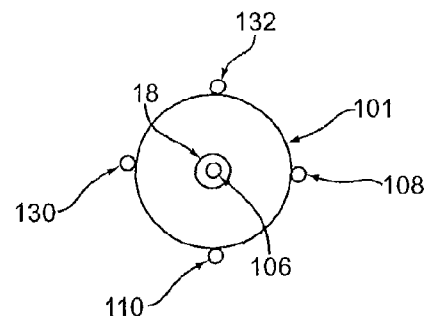
FIG. 2 shows a transverse cross-sectional view of the balloon catheter of FIG. 1 cut through balloon 101.

FIG. 2 illustrates a cross-sectional view across axis A-A' of the device shown in FIG. 1. Shaft 18 contains inflation lumen 106 in communication with balloon 101. Four cutting elements 108, 110, 130 and 132 overlay the surface of balloon 101. The cutting elements as illustrated have a substantially circular cross section. In such embodiments, upon inflation of the balloon, the cutting elements focus the radially directed force from the balloon to specific portions of the vessel wall and, hence, disrupt hardened plaque or other stenotic material.

The present invention also includes embodiments where the cutting elements, particularly the portion of the cutting element overlaying the working surface, include a sharpened edge or barbs positioned to contact the vessel wall upon inflation of the balloon. For example, the cutting elements may have a triangular of square cross section. Further examples of angioplasty balloon devices having cutting devices are disclosed in co-pending patent application Ser. No. 60/901,522, entitled "Balloon Catheter with Dilating Elements", filed Feb. 13, 2007, the contents of which are incorporated by reference.

The present invention also includes embodiments in which at least portions of the cutting device are covered by a layer of material, for example, a thin sheath including a polymer or other material. Such a covering shields covered portions of the cutting device from tissue and reduces the possibility of inadvertent damage to healthy tissue. Of course, the sheath must be sufficiently thin so as to allow the cutting element to focus radially directed force to specific portions of the vessel wall to disrupt hardened plaque or other stenotic material.

Materials Used for the Cutting Device and Balloon

The materials used to form the cutting device may be selected from a well-known list of suitable metals and polymeric materials. In certain embodiments, portions of the cutting device, for example, the central portion and the end portions can be formed from different materials. Suitable metals or metal alloys include stainless steels (e.g., 316, 316L or 304), nickel-titanium alloys including shape memory or superelastic types (e.g., nitinol or elastinite); inconel; noble metals including copper, silver, gold, platinum, palladium and iridium; refractory metals including Molybdenum, Tungsten, Tantalum, Titanium, Rhenium, or Niobium; stainless steels alloyed with noble and/or refractory metals; magnesium; amorphous metals; plastically deformable metals (e.g., tantalum); nickel-based alloys (e.g., including platinum, gold and/or tantalum alloys); iron-based alloys (e.g., including platinum, gold and/or tantalum alloys); cobalt-based alloys (e.g., including platinum, gold and/or tantalum alloys); cobalt-chrome alloys (e.g., elgiloy); cobalt-chromium-nickel alloys (e.g., phynox); alloys of cobalt, nickel, chromium and molybdenum (e.g., MP35N or MP20N); cobalt-chromium-vanadium alloys; cobalt-chromium-tungsten alloys; platinum-iridium alloys; platinum-tungsten alloys; magnesium alloys; titanium alloys (e.g., TiC, TiN); tantalum alloys (e.g., TaC, TaN); L605; magnetic ferrite; bioabsorbable materials, including magnesium; or other biocompatible metals and/or alloys thereof. One particularly preferred material is a self-expanding material such as the superelastic nickel-titanium alloy sold under the tradename NITINOL.

Other suitable materials used in the cutting device include carbon or carbon fiber, cellulose acetate, cellulose nitrate, silicone, polyethylene teraphthalate, polyurethane, polyamide, polyester, polyorthoester, polyanhydride, polyether sulfone, polyanhydride, polycarbonate, polypropylene, high molecular weight polyethylene, polylactic acid, polyglycolic acid, polytetrafluoroethylene, polycaprolactone, polyhydroxybutyrate valerate, a biodegradable polymer, or another biocompatible polymeric material, or mixtures or copolymers of these.

In one embodiment, the balloon portion of the balloon catheter is manufactured from a silicone. Other biocompatible materials can also be used. Such materials include, but are not limited to, biocompatible polymers such as polyethyleneterepthalate (PET), polyvinyl chloride, polypropylene, polyethylene, polyurethanes, nylons, polyesters, latex, natural rubber, synthetic rubber, elastomers and mixtures or copolymers of these materials.

In one embodiment, the balloon includes multiple layers of material. For example, the balloon can contain an inner most layer of PET, which provides a higher pressure balloon, surrounded by an outer layer of nylon, which provides a surface more resistant to puncture.

Delivery of the Bioactive

In certain embodiments, the bioactive is present on the surface of the cutting device or balloon, or is incorporated within the material of the cutting device or balloon.

Delivery of Bioactive from the Surface of or the Material of the Cutting Device or the Balloon In certain embodiments, one or more bioactives are present on the cutting device. In one embodiment, a bioactive is coated directly on the surface of one or more cutting elements (or on a primer layer, which is placed directly on the surface of the cutting element). In another embodiment, the bioactive is mixed with a carrier material and this mixture applied to the cutting element. In such a configuration, the release of the bioactive may be dependent on factors including the composition, structure and thickness of the carrier material. In one embodiment, the carrier material may contain pre-existing channels, through which the bioactive may diffuse, or channels created by the release of the bioactive, or another soluble substance, from the carrier material.

In certain embodiments, the carrier material and/or the barrier layer can include a bioelastomer, PLGA, PLA, PEG, Zein, or a hydrogel. In certain other embodiments, the carrier material and/or the barrier layer includes microcrystalline cellulose, hydroxypropylmethyl cellulose, hydroxypropyl cellulose, a cellulose product, a cellulose derivative, a polysaccharide or a polysaccharide derivative. In other embodiments the carrier material and/or the barrier layer includes lactose, dextrose, mannitol, a derivative of lactose, dextrose, mannitol, starch or a starch derivative. In other embodiments, the carrier material and/or the barrier layer includes a biostable or a biodegradable material, for example, a biostable or a biodegradable polymer. Examples of such biostable and biodegradable polymers are disclosed in U.S. Publication Number 2004-0243225A1, published Dec. 2, 2004, the contents of which are incorporated by reference.

In certain embodiments, one or more barrier layers may be deposited over the layer containing the bioactive. In other embodiments, a combination of one or more layers of bioactive, mixtures of carrier material/bioactive, and barrier layers are present. For example, the bioactive may be mixed with a carrier material and coated onto the cutting element and then over coated with a barrier layer(s). In yet other embodiments, multiple layers of bioactive, or mixtures of carrier material/bioactive, separated by barrier layers are present to form a multicoated cutting element. In certain embodiments, different bioactives are present in the different layers.

In other embodiments, the bioactive forms part of the structure of the cutting device itself. Alternatively, the cutting device may have holes, wells, slots, grooves, or the like for containing the bioactive, and/or mixtures of carrier material/bioactive, possibly separated by barrier layers. Illustrative medical devices having such configurations of bioactives coated on their surface are disclosed in U.S. Publication Number 2004-0243225A1, published Dec. 2, 2004, the contents of which are incorporated by reference.

In those embodiments where the bioactive is coated onto a surface of the cutting device, it may be advantageous to prepare the surface of the cutting device before depositing a coating thereon. Useful methods of surface preparation can include, but are not limited to cleaning; physical modifications such as etching, drilling, cutting, or abrasion; and chemical modifications such as solvent treatment, the application of primer coatings, the application of surfactants, plasma treatment, ion bombardment, covalent bonding and electrochemical methods such as electropolishing, striking, electroplating and electrochemical deposition. Such surface preparation may serve to activate the surface and promote the deposition or adhesion of the coating on the surface. Surface preparation can also selectively alter the release rate of the bioactive.

Any additional coating layers can similarly be processed to promote the deposition or adhesion of another layer, to further control the release of the bioactive, or to otherwise improve the biocompatibility of the surface of the layers. For example, plasma treating an additional coating layer before depositing a bioactive thereon may improve the adhesion of the bioactive, increase the amount of bioactive that can be deposited, and allow the bioactive to be deposited in a more uniform layer.

A primer layer, or adhesion promotion layer, may also be used with the present invention. This layer may comprise, for example, silane, acrylate polymer/copolymer, acrylate carboxyl and/or hydroxyl copolymer, polyvinylpyrrolidone/vinylacetate copolymer (PVP/VA), olefin acrylic acid copolymer, ethylene acrylic acid copolymer, epoxy polymer, polyethylene glycol, polyethylene oxide, polyvinylpyridine copolymers, polyamide polymers/copolymers polyimide polymers/copolymers, ethylene vinylacetate copolymer and/or polyether sulfones.

Figure 3:
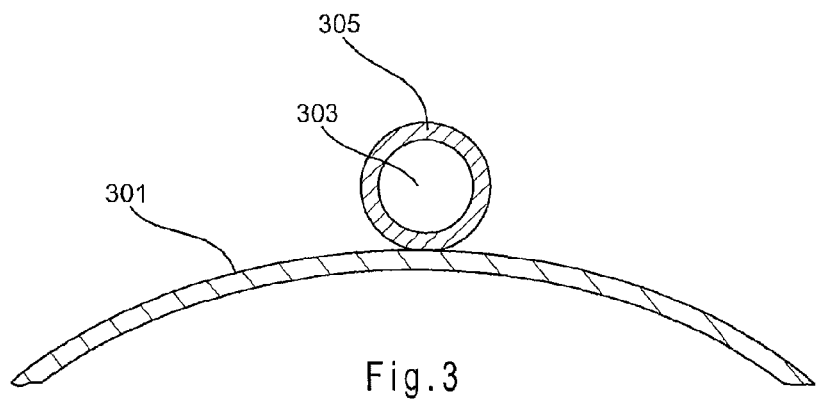
FIG. 3 is an expanded partial transverse cross-sectional view of balloon 101.
Figure 4:
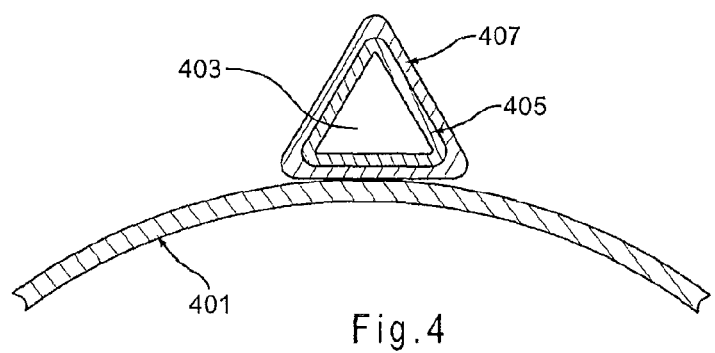
FIG. 4 is an expanded partial transverse cross-sectional view of an alternative embodiment of a balloon catheter.

FIG. 3 illustrates an expanded portion of the cross-sectional view shown in FIG. 2. Cutting device 303 is illustrated on the surface of balloon 301. Cutting device 303 is shown to have a substantially circular cross-section and to be coated with a layer of bioactive 305. FIG. 4 illustrates a similar expanded view of an embodiment in which cutting device 403 overlays the surface of balloon 401. In this embodiment, cutting device 403 has a substantially triangular cross section and is coated with a layer of bioactive 405 and a barrier layer 407.

Delivery of the Bioactive from Inside the Balloon

Figure 5:
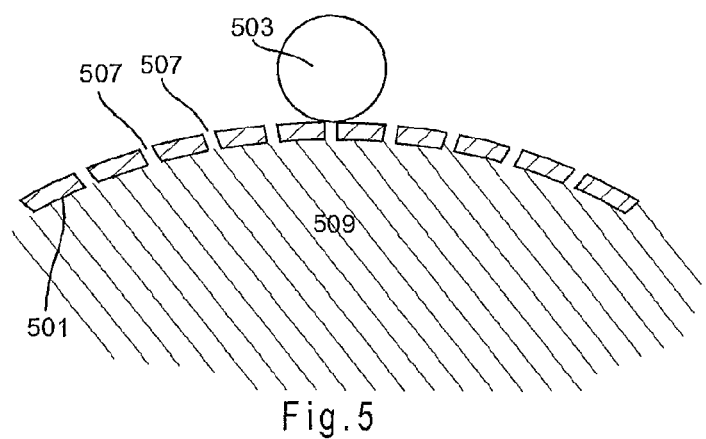
FIG. 5 is an expanded partial transverse cross-sectional view of an embodiment of a balloon catheter having pores.

In other embodiments of the present invention, one or more bioactives are contained within the inflatable balloon. In one such embodiment, a bioactive in contained within the fluid used to inflate the balloon and is released from the balloon through pores in the surface of the balloon. FIG. 5 illustrates a partial cross-sectional view across a balloon of such an embodiment. The interior 509 of balloon 501 includes an inflation fluid containing a bioactive. Any suitable inflation fluid may be used so long as it is compatible with delivery of the bioactive to the vessel wall. Suitable fluids include water for injection, isotonic saline or other sterile solutions. Polymeric hydrogels may also be used, especially where it is desired to increase the viscosity of the fluid.

The inflation fluid is released from the surface of the balloon though pores 507 upon inflation of the balloon. The number and size of the pores is chosen so that a pressure sufficient to inflate the balloon can be maintained while allowing limited escape of fluid, and bioactive, through the pores. In one embodiment, the pores are sized between approximately 0.01 microns and 500 microns. In other embodiments, the pores are sized between 0.1 microns and 100 microns. In yet other embodiments, the pores are sized between 1 micron and 10 microns.

Cutting element 503 is situated on the surface of balloon 501. In certain embodiments, the density of pores in the balloon surface varies with position, for example, the pores may be concentrated in areas adjacent to the cutting element.

Figure 6:
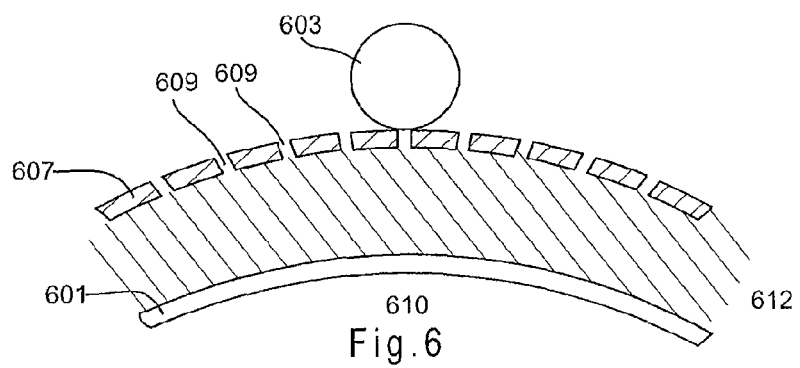
FIG. 6 is an expanded partial transverse cross-sectional view of an embodiment of a double balloon catheter where the outer balloon includes pores.

FIG. 6 illustrates a partial cross-sectional view across the working surface in another embodiment of the present invention. This embodiment includes an inner balloon and an outer balloon. The interior 610 of inner balloon 601 is in fluid communication with an inflation lumen that delivers an inflation fluid to the balloon. Inner balloon 601 is impermeable to the inflation fluid and is situated inside outer balloon 607. Cutting element 603 overlies the outside surface of outer balloon 607. Intermediate space 612 between inner balloon 601 and outer balloon 607 is in fluid contact with a delivery lumen, such as the lumen 140 illustrated in FIG. 1. Fluid containing one or more bioactives can be introduced into intermediate space 612 via the delivery lumen. Outer balloon 607 contains pores 609 through which the bioactives are delivered to the outside surface of the balloon and hence to the vessel wall. In one embodiment, the delivery lumen allows for replenishment of bioactives from the proximal end of the device when the distal end of the device is placed within a body vessel.

Figure 7:
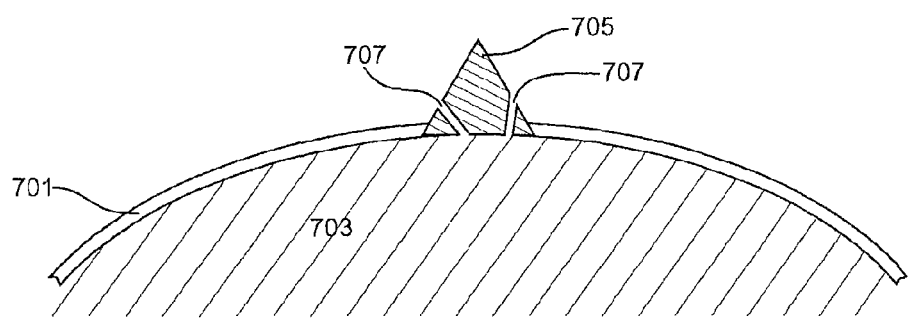
FIG. 7 is an expanded partial transverse cross-sectional view of an embodiment of a balloon catheter including a cutting element having a channel.

In another embodiment of the present invention, one or more bioactives are delivered through holes in at least one of the cutting elements. FIG. 7 illustrates a cross-sectional view across the working surface of a balloon of one such embodiment. Cutting element 705 is either attached to the surface of balloon 701 or is at least partially imbedded within the balloon material. Cutting element 705 contains at least one channel 707 providing fluid communication between the interior 703 of the balloon and the exterior of the device. In another embodiment, the device includes two balloons, one within the other. The cutting element is attached to the outer balloon and the fluid containing the bioactive is present within an intermediate lumen between the outer balloon and an inner balloon. The interior of the inner balloon is in fluid communication with an inflation lumen, while the intermediate lumen is in fluid communication with a bioactive delivery lumen.

In another embodiment, at least one bioactive is positioned within the material of the balloon. For example, the bioactive can be mixed with a polymer and extruded to form the balloon. Such a method of manufacture is suitable for those bioactives that are stable under the conditions, particularly the temperature, required for the extrusion process. For example, in one embodiment, a powered base silicone material is mixed with the bioactive in a solvent. The mixture is then extruded at low temperatures with the solvent evaporating as the silicone material cures. Low temperature silicone is utilized so as not to evaporate or inactivate the bioactive.

In another embodiment, a bioactive is imbibed into the material of the balloon. U.S. Pat. No. 5,624,704, which is hereby incorporated by reference, teaches such methods of incorporating a bioactive into the material of a non-metallic device. Briefly, the device is contacted with a solvent containing the bioactive and a penetrating agent. In one embodiment, an alkalinizing agent is added to enhance the reactivity of the material of the device. The solvent is preferably an organic solvent and the penetrating agent is an ingredient that enables the bioactive to permeate the base material of the device and to become deposited within the device.

Examples of suitable organic solvents include, but are not limited to, alcohols (i.e. methanol, ethanol), ketones (acetone, methylethylketone), ethers (tetrahydrofuran), aldehydes (formaldehyde), acetonitrile, acetic acid, methylene chloride and chloroform. The penetrating agent can be any compound that can be used to promote penetration of the bioactive into the material of the device. Examples of suitable compounds are esters (i.e. ethyl acetate, propyl acetate, butyl acetate, amyl acetate, and combinations thereof), ketones (i.e. acetone and methylethylketone), methylene chloride and chloroform. The alkalinizing agent can be an organic and inorganic base including sodium hydroxide, potassium hydroxide, ammonia in water (27% ammonium hydroxide), diethylamine and triethylamine. A high ionic strength salt may act both as an alkalinizing agent and as a penetrating agent. Such salts include sodium chloride, potassium chloride and ammonium acetate.

In another embodiment, the bioactive is applied to the outside surface of the balloon. For example, the bioactive may be applied by spraying, dipping, pouring, pumping, brushing, wiping, vacuum deposition, vapor deposition, plasma deposition, electrostatic deposition, ultrasonic deposition, epitaxial growth, electrochemical deposition or any other method known to those skilled in the art. The bioactive may be applied as a separate layer or may be included in a layer also including a carrier material as described below.

In one embodiment, a bioactive is placed directly on the surface of the balloon and forms the outermost coating layer on the balloon. In another embodiment, the bioactive is coated onto the balloon and one or more barrier layers are placed over at least a portion of the bioactive.

In yet another embodiment, the bioactive is mixed with a carrier material and this mixture applied to the balloon. Alternatively, the carrier material may be applied to the surface of the balloon and the bioactive absorbed into the carrier material. In such configurations, the release of the bioactive may be dependent on factors including the composition, structure and thickness of the carrier material. In one embodiment, the carrier material may contain pre-existing channels, through which the bioactive may diffuse, or channels created by the release of the bioactive, or another soluble substance, from the carrier material.

In other embodiments of the invention, a combination of one or more layers of bioactive, mixtures of carrier material/bioactive, and barrier layers are present on the surface of the balloon. For example, the bioactive may be mixed with a carrier material and coated onto the balloon and then overcoated with one or more barrier layer(s). In yet other embodiments, multiple layers of bioactive, or mixtures of carrier material/bioactive, possibly separated by barrier layers, are present to form a multicoated balloon. In certain embodiments, different bioactives are present in the different layers.

In certain embodiments of the invention, the carrier material and/or the barrier layer comprise a biocompatible polymer. Such polymers include both biostable and biodegradable polymers. Selection of the appropriate polymer for use in the present invention may depend upon the desired rate of release of the bioactive, the porosity of the polymer, and the rate of degradation of the polymer, for example. The coating compositions of the present invention may also include additives, such as diluents, excipients, stabilizers or the like.

In another embodiment, an absorbable mesh is attached to the outside surface of the balloon and the bioactive is absorbed into this mesh. Examples of suitable mesh include mesh cotton cellulose or derivative of cellulose, cotton, cotton derivatives, alginates, dextran and rayon. Such materials may be chosen to absorb body fluids which they come into contact with and in doing so to swell and release the bioactive.

Bioactives

In one embodiment of the invention, the bioactive is an antithrombogenic agent. Devices comprising an antithrombogenic agent are particularly preferred for implantation in areas of the body that contact blood. An antithrombogenic agent is any agent that inhibits or prevents thrombus formation within a body vessel. Types of antithrombotic agents include anticoagulants, antiplatelets, and fibrinolytics. Examples of antithrombotics include but are not limited to anticoagulants such as thrombin, Factor Xa, Factor VIIa and tissue factor inhibitors; antiplatelets such as glycoprotein IIb/IIIa, thromboxane A2, ADP-induced glycoprotein IIb/IIIa, and phosphodiesterase inhibitors; and fibrinolytics such as plasminogen activators, thrombin activatable fibrinolysis inhibitor (TAFI) inhibitors, and other enzymes which cleave fibrin.

Further examples of antithrombotic agents include anticoagulants such as heparin, low molecular weight heparin, covalent heparin, synthetic heparin salts, coumadin, bivalirudin (hirulog), hirudin, argatroban, ximelagatran, dabigatran, dabigatran etexilate, D-phenalanyl-L-poly-L-arginyl, chloromethy ketone, dalteparin, enoxaparin, nadroparin, danaparoid, vapiprost, dextran, dipyridamole, omega-3 fatty acids, vitronectin receptor antagonists, DX-9065a, CI-1083, JTV-803, razaxaban, BAY 59-7939, and LY-51,7717; antiplatelets such as eftibatide, tirofiban, orbofiban, lotrafiban, abciximab, aspirin, ticlopidine, clopidogrel, cilostazol, dipyradimole; fibrinolytics such as alfimeprase, alteplase, anistreplase, reteplase, lanoteplase, monteplase, tenecteplase, urokinase, streptokinase, or phospholipid encapsulated microbubbles; and other bioactive agents such as endothelial progenitor cells or endothelial cells.

Another example of an antithrombotic agent is a nitric oxide source such as sodium nitroprussiate, nitroglycerin, S-nitroso and N-nitroso compounds. In one embodiment, a material capable of releasing nitric oxide from blood-contacting surfaces can be delivered by the device of the invention. Examples of such materials include, but are not limited to, those described in U.S. publication number 200410224868A1, published Nov. 11, 2004, and 2002/0115559A1, published Aug. 22, 2002, the contents of which are incorporated by reference.

Other examples of bioactive agents suitable for inclusion in the devices of the present invention include antiproliferative/antimitotic agents including natural products such as vinca alkaloids (vinblastine, vincristine, and vinorelbine), paclitaxel, rapamycin analogs, epidipodophyllotoxins (etoposide, teniposide), antibiotics (dactinomycin (actinomycin D) daunorubicin, doxorubicin and idarubicin), anthracyclines, mitoxantrone, bleomycins, plicamycin (mithramycin) and mitomycin, enzymes (for example, L-asparaginase which systemically metabolizes L-asparagine and deprives cells which do not have the capacity to synthesize their own asparagine); antiplatelet agents such as (GP) $II_b/III_a$ inhibitors and vitronectin receptor antagonists; antiproliferative/antimitotic alkylating agents such as nitrogen mustards (mechlorethamine, cyclophosphamide and analogs, melphalan, chlorambucil), ethylenimines and methylmelamines (hexamethylmelamine and thiotepa), alkyl sulfonates-busulfan, nirtosoureas (carmustine (BCNU) and analogs, streptozocin), trazenes-dacarbazinine (DTIC); antiproliferative/antimitotic antimetabolites such as folic acid analogs (methotrexate), pyrimidine analogs (fluorouracil, floxuridine, and cytarabine), purine analogs and related inhibitors (mercaptopurine, thioguanine, pentostatin and 2-chlorodeoxyadenosine {cladribine}); platinum coordination complexes (cisplatin, carboplatin), procarbazine, hydroxyurea, mitotane, aminoglutethimide; hormones (i.e. estrogen); anticoagulants (heparin, synthetic heparin salts and other inhibitors of thrombin); fibrinolytic agents (such as tissue plasminogen activator, streptokinase and urokinase), aspirin, dipyridamole, ticlopidine, clopidogrel, abciximab; antimigratory; antisecretory (breveldin); anti-inflammatory: such as adrenocortical steroids (cortisol, cortisone, fludrocortisone, prednisone, prednisolone, 6α-methylprednisolone, triamcinolone, betamethasone, and dexamethasone), non-steroidal agents (salicylic acid derivatives i.e. aspirin; para-aminophenol derivatives i.e. acetaminophen; indole and indene acetic acids (indomethacin, sulindac, and etodalac), heteroaryl acetic acids (tolmetin, diclofenac, and ketorolac), arylpropionic acids (ibuprofen and derivatives), anthranilic acids (mefenamic acid, and meclofenamic acid), enolic acids (piroxicam, tenoxicam, phenylbutazone, and oxyphenthatrazone), nabumetone, gold compounds (auranofin, aurothioglucose, gold sodium thiomalate); immunosuppressives (cyclosporine, tacrolimus (FK-506), sirolimus (rapamycin), tacrolimus, everolimus, azathioprine, mycophenolate mofetil); angiogenic agents: vascular endothelial growth factor (VEGF), fibroblast growth factor (FGF); angiotensin receptor blockers; nitric oxide and nitric oxide donors; antisense oligionucleotides and combinations thereof; cell cycle inhibitors, mTOR inhibitors, and growth factor receptor signal transduction kinase inhibitors; retenoids; cyclin/CDK inhibitors; endothelial progenitor cells (EPC); angiopeptin; pimecrolimus; angiopeptin; HMG co-enzyme reductase inhibitors (statins); metalloproteinase inhibitors (batimastat); protease inhibitors; antibodies, such as EPC cell marker targets, CD34, CD133, and AC 133/CD133; Liposomal Biphosphate Compounds (BPs), Chlodronate, Alendronate, Oxygen Free Radical scavengers such as Tempamine and PEA/NO preserver compounds, and an inhibitor of matrix metalloproteinases, MMPI, such as Batimastat. Still other bioactive agents that can be incorporated in or coated on a frame include a PPAR α-agonist, a PPAR δ agonist and RXR agonists, as disclosed in published U.S. Patent Application US2004/0073297 to Rohde et al., published on Apr. 15, 2004 and incorporated in its entirety herein by reference.

In a preferred embodiment of the present invention, the bioactive is paclitaxel, rapamycin, a rapamycin derivative, an antisense oligonucleotide, or a mTOR inhibitor.

Device Delivery and Methods of Treating a Patient

Another aspect of the present invention provides methods for delivering the devices described herein to any suitable body vessel. The devices can be delivered to any suitable body vessel, including a vein, artery, biliary duct, ureteral vessel, body passage or portion of the alimentary canal. While many preferred embodiments discussed herein discuss devices having application in the treatment of stenosis or restenosis, other embodiments provide for delivery to other body vessels. In another matter of terminology there are many types of body canals, blood vessels, ducts, tubes and other body passages, and the term "vessel" is meant to include all such passages.

In some embodiments, devices of the present invention having a compressed delivery configuration with a very low profile, small collapsed diameter and great flexibility, may be able to navigate small or tortuous paths through a variety of body vessels. A low-profile device may also be useful in coronary arteries, carotid arteries, vascular aneurysms, and peripheral arteries and veins (e.g., renal, iliac, femoral, popliteal, sublavian, aorta, intercranial, etc.). Other nonvascular applications include gastrointestinal, duodenum, biliary ducts, esophagus, urethra, reproductive tracts, trachea, and respiratory (e.g., bronchial) ducts.

In certain embodiments, the device of the invention is used to treat a narrowing of a peripheral artery or vein. Examples of such arteries include, but are not limited to, the femoral artery, the superficial femoral artery (artery below the branch for the profunda femoris artery), the popliteal artery and the infrapopliteal artery. Examples of such veins include, but are not limited to, the femoral vein, the popliteal vein and the lesser/greater saphenous vein. Another application of the device is to open up arteriovenous fistulas that have occluded due to thrombus formation. When used to treat thrombosis, the device of the invention can also deliver an anti-coagulant.

For example, the device of the present invention can be compressed to a delivery configuration within a retaining sheath that is part of a delivery system, such as a catheter-based system. Upon delivery, the device can be expanded, for example, by removing the sheath and then inflating the balloon portion of the device. The delivery configuration can be maintained prior to deployment of the device by any suitable means, including a sheath, a suture, a tube or other restraining material around all or part of the device.

The device of the invention may be deployed according to well-known deployment techniques for expandable medical devices. For example, the device is positioned at the distal end of a catheter with a lubricous sleeve placed over the valve prosthesis to hold the medical device in a contracted state with a relatively small diameter. The device may then be delivered to the point of treatment by advancing the catheter over a guidewire to the location of the lesion and then withdrawing the sleeve from over the device. The balloon is then expanded to bring the outside surface of the working surface, and the cutting elements, into contact with the vessel wall. Further expansion of the balloon causes the cutting elements to breakup any hardened plague on the vessel wall, allowing further expansion of the vessel.

Expansion of the balloon also results in a therapeutically-effective amount of a bioactive being delivered to the vessel wall. The bioactive may be delivered either on the cutting device or within or on the surface of the balloon. In various embodiments, at least 90 percent of the bioactive present on the cutting device or on or within the material of the balloon catheter is released into an aqueous physiological environment within 30 sec, 1 minute, 2 minutes, 5 minutes, 10 minutes, 15 minutes, 20 minutes, 30 minutes, 45 minutes, 60 minutes or 90 minutes.

In those embodiments where the bioactive is contained within a fluid in the interior of the balloon, the bioactive may be delivered to the vessel wall over similar time periods. Of course, such embodiments allow for continuous delivery of the bioactive from the proximal end of the catheter while the distal end is positioned within a body vessel. After expansion of the vessel and delivery of the bioactive, the balloon is deflated and the catheter removed from the vessel.

In certain configurations, a rapid exchange delivery balloon catheter allows exchange from a balloon angioplasty catheter to a prosthesis delivery catheter without the need to replace the angioplasty catheter guide wire with an exchange-length wire guide before exchanging the catheters. Such delivery methods are described in U.S. Pat. Nos. 5,690,642, 5,814,061 and 6,371,961, the contents of which are incorporated by reference.

While preferred embodiments of the invention have been described, it should be understood that the invention is not so limited, and modifications may be made without departing from the invention. The scope of the invention is defined by the appended claims, and all devices that come within the meaning of the claims, either literally or by equivalence, are intended to be embraced therein. Furthermore, the advantages described above are not necessarily the only advantages of the invention, and it is not necessarily expected that all of the described advantages will be achieved with every embodiment of the invention.

I claim:

1. A balloon catheter comprising:
a shaft having a distal end and a proximal end;
an expandable inner balloon mounted at the distal end of the shaft, the shaft having an inflation lumen extending therethrough and in fluid communication with an interior region of the inner balloon,
an expandable outer balloon positioned around the inner balloon and defining an intermediate region between the inner balloon and the outer balloon, the shaft having a delivery lumen extending therethrough and in fluid communication with the intermediate region, and
a cutting element positioned on an exterior surface of the outer balloon; wherein the cutting element comprises a blade extending at least substantially the length of the exterior surface parallel to an axis extending from the distal end to the proximal end or circumventing the exterior surface in a helical or serpentine form,
wherein the outer balloon further comprises a plurality of pores positioned separate from the cutting element and providing fluid communication between the intermediate region and the exterior of the balloon catheter.

2. The balloon catheter of claim 1, further comprising a bioactive, wherein the bioactive is contained in the intermediate region.

3. The balloon catheter of claim 2, wherein the bioactive is selected from the group consisting of paclitaxel, rapamycin, a rapamycin derivative, an antisense oligonucleotide, and a mTOR inhibitor.

4. The balloon catheter of claim 3, wherein the bioactive is paclitaxel.

5. The balloon catheter of claim 2, wherein the bioactive is selected from the group consisting of an antiproliferative agent, an antimitotic agent, an antibiotic, a hormone, an anti-inflammatory agent, an immunosuppressive agent, an antibody, a statin, an endothelial progenitor cell and an endothelial cell.

6. The balloon catheter of claim 1, wherein the density of the plurality of pores in the surface of the outer balloon varies with position.

7. The balloon catheter of claim 6, wherein the density of pores is higher in regions closest to the cutting element.

8. The balloon catheter of claim 1, wherein the cutting element comprises a material selected from the group consisting of stainless steel, nickel, silver, platinum, palladium, gold, titanium, tantalum, iridium, tungsten, and a superelastic nickel-titanium alloy.

9. The balloon catheter of claim 1, wherein the cutting element comprises a material selected from the group consisting of carbon, carbon fiber, cellulose acetate, cellulose nitrate, silicone, polyethylene teraphthalate, polyurethane, polyamide, polyester, polyorthoester, polyanhydride, polyether sulfone, polyanhydride, polycarbonate, polypropylene, high molecular weight polyethylene, polylactic acid, polyglycolic acid, polytetrafluoroethylene, polycaprolactone, polyhydroxybutyrate valerate, a biodegradable polymer, a biocompatible polymeric material, and mixtures and copolymers thereof.

10. The balloon catheter of claim 9, wherein the cutting element a biocompatible polymeric material.

11. The balloon catheter of claim 1, wherein at least one of the outer balloon and the inner balloon comprises a material selected from the group consisting of silicone, a biocompatible polymer, polyethyleneterepthalate, polyvinyl chloride, polypropylene, polyethylene, polyurethane, nylon, polyester, latex, natural rubber, synthetic rubber, an elastomer and mixtures and copolymers thereof.

12. The balloon catheter of claim 1, wherein at least one of the plurality of pores is sized between 0.01 and 500 microns.

13. The balloon catheter of claim 12, wherein at least one of the plurality of pores is sized between 0.1 and 100 microns.

14. The balloon catheter of claim 1, wherein the cutting element is partially embedded in a wall of the outer balloon.

15. A balloon catheter comprising:
a shaft having a distal end and a proximal end;
an expandable inner balloon mounted at the distal end of the shaft, the shaft having an inflation lumen extending therethrough and in fluid communication with an interior region of the inner balloon,
an expandable outer balloon positioned around the inner balloon and defining an intermediate region between the inner balloon and the outer balloon, the shaft having a delivery lumen extending therethrough and in fluid communication with the intermediate region,
a cutting element positioned on an exterior surface of the outer balloon, wherein the cutting element comprises a blade extending at least substantially the length of the exterior surface parallel to an axis extending from the distal end to the proximal end or circumventing the exterior surface in a helical or serpentine form and wherein the blade comprises a biocompatible polymer, and
a fluid comprising a bioactive positioned within the intermediate region,
wherein the outer balloon comprises a plurality of pores positioned separate from the cutting element and providing fluid communication between the intermediate region and the exterior of the balloon catheter.

16. The balloon catheter of claim 15, wherein the bioactive is selected from the group consisting of an antiproliferative agent, an antimitotic agent, an antibiotic, a hormone, an anti-inflammatory agent, an immunosuppressive agent, an antibody, a statin, an endothelial progenitor cell and an endothelial cell.

17. The balloon catheter of claim 15, wherein the cutting element and the outer balloon comprise a biocompatible polymer.

* * * * *